US012667820B2

(12) United States Patent　　(10) Patent No.: US 12,667,820 B2
Spieker et al.　　　　　　　　　　(45) Date of Patent: Jun. 30, 2026

(54) PROCESS AND APPARATUS FOR CONTACTING FEED AND CATALYST WITH IMPROVED FLUID DYNAMICS

(71) Applicant: UOP LLC, Des Plaines, IL (US)

(72) Inventors: Wolfgang A. Spieker, Glenview, IL (US); Richard A. Johnson, II, Algonquin, IL (US)

(73) Assignee: UOP LLC, Rosemont, IL (US)

(*) Notice: Subject to any disclaimer, the term of this patent is extended or adjusted under 35 U.S.C. 154(b) by 1142 days.

(21) Appl. No.: 17/556,818

(22) Filed: Dec. 20, 2021

(65) Prior Publication Data

US 2023/0191354 A1　　Jun. 22, 2023

(51) Int. Cl.
*B01J 19/00* (2006.01)
*B01J 8/02* (2006.01)
*C07C 5/333* (2006.01)
*C01B 3/38* (2006.01)

(52) U.S. Cl.
CPC ......... *B01J 19/0093* (2013.01); *B01J 8/0278* (2013.01); *C07C 5/333* (2013.01); *B01J 2219/00835* (2013.01); *C01B 3/38* (2013.01)

(58) Field of Classification Search
CPC .... C07C 5/333; B01J 19/00; B01J 8/02; B01J 8/0278; B01J 19/0093
See application file for complete search history.

(56) References Cited

U.S. PATENT DOCUMENTS

| | | | |
|---|---|---|---|
| 9,023,285 B2 * | 5/2015 | Davydov | ............. C07C 5/3335 |
| | | | 422/216 |
| 10,307,721 B2 * | 6/2019 | Li | ........................... B01J 8/0065 |
| 2010/0025295 A1 * | 2/2010 | Mehlberg | ............... B01D 45/12 |
| | | | 95/35 |
| 2010/0236985 A1 * | 9/2010 | Luo | ........................ C07C 5/3337 |
| | | | 208/138 |
| 2014/0140895 A1 | 5/2014 | Davydov et al. | |
| 2022/0081373 A1 * | 3/2022 | Doosa | ..................... B01J 37/16 |
| 2022/0333018 A1 | 10/2022 | Senetar et al. | |

FOREIGN PATENT DOCUMENTS

| | | |
|---|---|---|
| CN | 1345911 A | 4/2002 |
| CN | 107974286 A | 5/2018 |

OTHER PUBLICATIONS

Search Report and Written Opinion for PCT/US2022/081667 dated May 2, 2023.

* cited by examiner

*Primary Examiner* — Sharon Pregler
(74) *Attorney, Agent, or Firm* — Paschall & Associates, LLC; James C. Paschall

(57)　　　　ABSTRACT

A process and apparatus comprise a reaction chamber that includes an aspect ratio between about 0.7 and 1.3 for establishing a dense catalyst bed in the reaction chamber while minimizing hot residence time of the product gas in a range that will not deteriorate product selectivity. We have found the dense catalyst bed is necessary to ensure sufficient contact between catalyst and feed gas.

18 Claims, 3 Drawing Sheets

PROCESS AND APPARATUS FOR CONTACTING FEED AND CATALYST WITH IMPROVED FLUID DYNAMICS

FIELD

The field is the reaction of feed with fluid catalyst. The field may particularly relate to reacting a feed with a fluid catalyst to catalyze an endothermic reaction.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion.

Dehydrogenation catalyst may incorporate a dehydrogenation metal such as gallium with a molecular sieve or an amorphous material. The catalyst must be sufficiently robust and appropriately sized to be able to resist the attrition expected in a fluidized system.

In PDH reactions with fluidized catalyst, coke can deposit on the catalyst while catalyzing the reaction. The catalyst may be regenerated in a catalyst regenerator by combusting coke from the catalyst in the presence of oxygen. In some cases, additional fuel may be combusted in the regenerator to increase the temperature of the regenerated catalyst. The hot regenerated catalyst may then be transferred back to the reactor to catalyze the reaction. If insufficient heat is provided to drive the endothermic reaction, the conversion to desired products will be lower than desired. The extent of conversion therefore relies on the amount of heat introduced to the reaction.

For a given temperature in the regenerator, additional heat can be provided to the reaction through increased catalyst circulation and by increasing the temperature of regenerated catalyst. The drawback of increased regeneration temperature is, however, that contacting feed with regenerated catalyst at higher temperature leads to additional thermal cracking reactions. Catalytic reactions are more selective to the desired products than thermal cracking reactions. Care must be taken to maximize catalytic reactions over thermal cracking reactions. Maximizing catalytic reactions requires promoting thorough contact between catalyst and reactant feed.

There is a need, therefore, for improved processes and apparatuses for thoroughly contacting catalyst with paraffin feed to maximize catalytic reactions over thermal reactions to improve product selectivity.

BRIEF SUMMARY

A process and apparatus comprise a reaction chamber that includes an aspect ratio between about 0.7 and 1.3 for establishing a dense catalyst bed in the reaction chamber while minimizing a hot residence time of the product gas with catalyst in a range that will not deteriorate product selectivity.

DEFINITIONS

Figure 1:
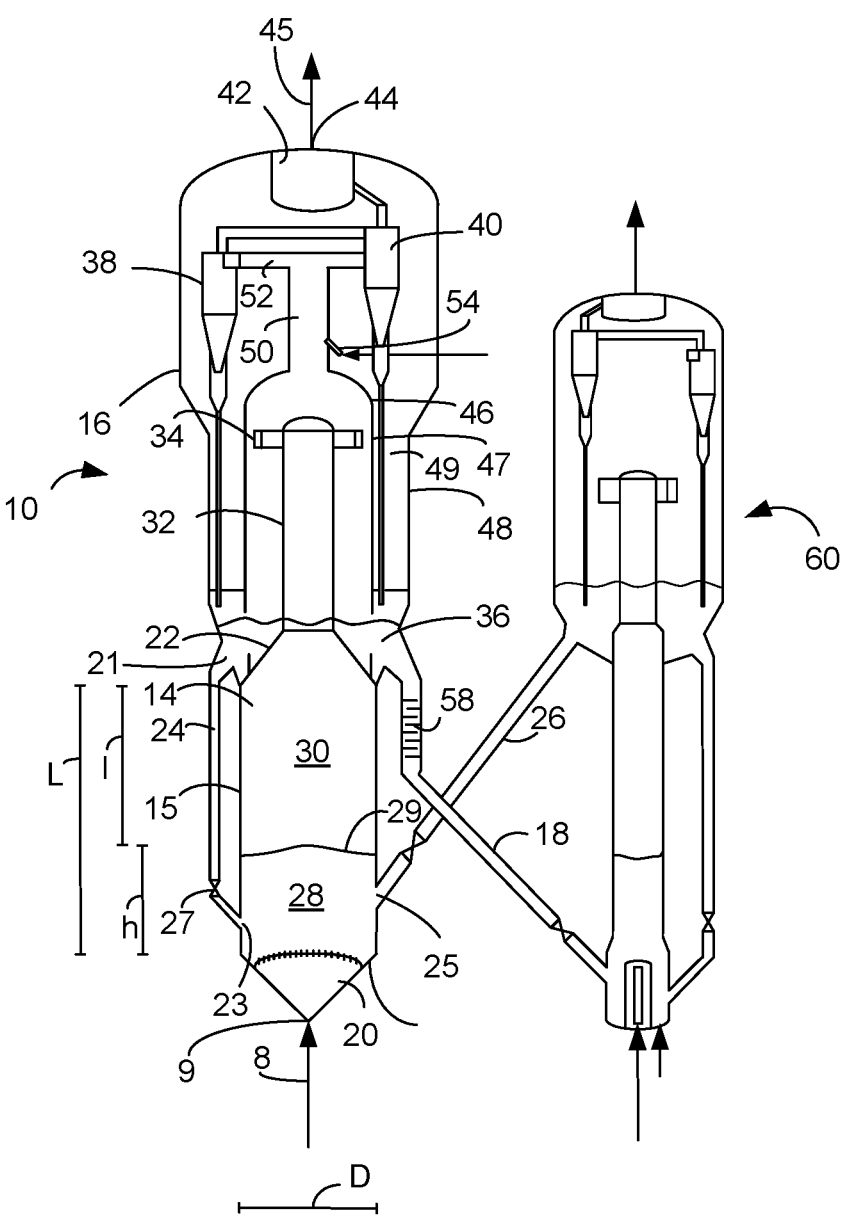
FIG. 1 is a schematic drawing of a process and apparatus of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

DETAILED DESCRIPTION

In fluidized paraffin dehydrogenation (PDH), paraffinic feed is contacted with fluidized catalyst typically in a fast fluidized flow regime. After the feed is contacted with catalyst in a dense catalyst bed, non-selective reactions such as thermal cracking reactions continue in a dilute phase that reduce the overall selectively of the paraffin dehydrogenation process. The residence of product gas with catalyst at reaction temperature in the dilute phase is considered "hot residence time". A process to reduce the hot residence time in the dilute phase can improve the selectively to the desired propylene and overall economics of the unit. However, reducing residence time in a fast fluidized flow regime can have other adverse effects on the fluid dynamics. As the distance from the top of the dense catalyst bed to the transition section of the reaction chamber is decreased, the dense catalyst bed deteriorates and contact between feed and catalyst suffers greatly. Without a stable dense catalyst bed, feed can bypass the catalyst resulting in major reductions in conversion of feed and selectivity to desired product.

Product selectivity is dependent on hot gas residence time in the reactor. Product selectivity falls over time in the reactor as the product gas travels above the dense catalyst bed. The objective is to minimize hot gas residence time in the reactor in order to preserve product selectivity.

We have discovered a process and apparatus that maintains a dense catalyst bed while minimizing hot gas residence time. PDH catalyst is used in a dehydrogenation reaction process to catalyze the dehydrogenation of paraffins, such as ethane, propane, iso-butane, and n-butane, to olefins, such as ethylene, propylene, isobutene and n-butenes, respectively. The PDH process will be described exemplarily to illustrate the disclosed apparatus and process.

The conditions in the dehydrogenation reactor may include a temperature of about 500 to about 800° C., a pressure of about 40 to about 310 kPa and a catalyst to oil ratio of about 5 to about 100. The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated.

An exemplary PDH reactor 10 is shown in FIG. 1. The PDH reactor 10 may comprise two chambers, a reaction chamber 14 and a separation chamber 16. A feed line 8 may charge a feed stream of paraffins to the reactor 10 through a feed inlet 9. The feed stream may predominantly comprise propane or butane, but other paraffins such as ethane may be present in the feed stream in conjunction with or to the exclusion of other paraffins. Any suitable feed distributor can be used to distribute the feed stream to the reactor 10. A domed feed distributor 20 may be utilized in the reaction chamber 14 of the reactor 10. The domed feed distributor 20 receives a gaseous paraffinic feed stream and distributes the feed stream through nozzles in the top dome of the domed reactant distributor 20 to distribute the feed stream across the entire cross section of the reaction chamber 14. It is envisioned that other fluidizing gases may be used to also promote fluidization in the reaction chamber 14. In an embodiment, the distributed feed stream and catalyst ascend in the reaction chamber 14 and the reactor 10.

A recycle catalyst pipe 24 has an outlet end comprising a first catalyst inlet 23 which in an embodiment may be connected to and in upstream communication with the reaction chamber 14. The recycle catalyst pipe 24 passes a first stream of recycled spent catalyst that has not undergone regeneration through the outlet end and the first catalyst inlet 23 to the reaction chamber 14 in an embodiment. The recycle catalyst pipe 24 recycles spent catalyst to the reaction chamber 14 through the first catalyst inlet 23.

A second catalyst inlet 25 delivers a second catalyst stream to the reactor 10. A regenerated catalyst pipe 26 is in downstream communication with a catalyst regenerator 60. The regenerated catalyst pipe 26 passes a second stream of regenerated catalyst from a regenerator 60 to the second catalyst inlet 25. The second catalyst inlet 25 provides regenerated catalyst to the reaction chamber 14. The second catalyst inlet 25 may be spaced apart and may be above the first catalyst inlet 23.

The reaction chamber 14 comprise a vertical wall 15 which may be cylindrical. The vertical wall extends between two graduated sections of decreasing inner diameters moving away from the vertical wall: a bottom distribution section 12 and an upper transition section 22. The distance L of the vertical wall 15 between the distribution section 12 and the transition section 22 comprises the length of the reaction chamber 14. The reaction chamber also has an inner diameter D. If the cross section of the reaction chamber 14 is not circular, the inner diameter D is the widest lateral dimension between opposing sides. In the reaction chamber 14 the first stream of catalyst and the second stream of catalyst mix together in a dense bed 28 of mixed catalyst having an upper interphase 29. The height of dense catalyst bed may be adjusted via catalyst recycle through the first catalyst inlet 23 to achieve the desired weight hourly space velocity (WHSV). Ideally there should be a density profile along the height of the reaction chamber which has a constant density over height in the bottom of the reaction chamber.

The feed stream is contacted with the catalyst in the dense bed 28, and the reactant paraffins undergo endothermic conversion to olefins, typically propane to propylene. The feed stream and the catalyst rise from the dense bed 28 in the reaction chamber 14 of the reactor 10 impelled by the feed stream continually entering the reactor and molar expansion and enter into a dilute phase 30.

At an interface 29, the fluid dynamics transition from a dense bed 28 of catalyst below the interface to a fast-fluidized flow regime in the dilute phase region 30. The catalyst density in the dense bed of catalyst is about 320 kg/m$^3$ (20 lb/ft$^3$) to about 480 kg/m$^3$ (30 lb/ft$^3$); whereas the catalyst density in the dilute phase is about 100 kg/m$^3$ (6.3 lb/ft') to about 160 kg/m$^3$ (10 lb/ft). The superficial velocity of the feed stream and the stream of mixed catalyst ascending in the reaction chamber 14 will typically be at least about 1.2 m/s (4 ft/s) to about 2.4 m/s (8 ft/s) to provide the fast-fluidized flow regime. The gaseous feed stream and mixed catalyst ascend in a fast-fluidized flow regime in which catalyst may slip relative to the gas and the gas can take indirect upward trajectories.

The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An exemplary embodiment of a catalyst includes alumina or silica-alumina containing gallium, a noble metal, and an alkali or alkaline earth metal.

The catalyst support comprises a carrier material, a binder and an optional filler material to provide physical strength and integrity. The carrier material may include alumina or silica-alumina. Silica sol or alumina sol may be used as the binder. The alumina or silica-alumina generally contains alumina of gamma, theta and/or delta phases. The catalyst support particles may have a nominal diameter of about 20 to about 200 micrometers with the average diameter of about 50 to about 150 micrometers. Preferably, the surface area of the catalyst support is 85-140 m$^2$/g.

The dehydrogenation catalyst may comprise a dehydrogenation metal on a support. The dehydrogenation metal may be a one or a combination of transition metals. A noble metal may be a preferred dehydrogenation metal such as platinum or palladium. Gallium is an effective metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.001% to 10 wt % metals may be incorporated into the catalyst. In the case of the noble metals, it is preferred to use about 10 parts per million (ppm) by weight to about 600 ppm by weight noble metal. More preferably it is preferred to use 10-100 ppm by weight noble metal. The preferred noble metal is platinum. Gallium should be present in the range of 0.3 wt % to about 3 wt %, preferably about 0.5 wt % to about 2 wt %. Alkali and alkaline earth metals are present in the range of about 0.05 wt % to about 1 wt %.

The feed stream lifts a mixed stream of catalyst comprising the first stream of catalyst mixed with the second stream of catalyst upwardly in the reaction chamber while paraffins convert to olefins in the presence of the dehydrogenation catalyst. The catalyst gradually becomes spent catalyst attributed to the agglomeration of coke deposits on the catalyst. A fluidizing inert gas may be distributed to the reaction chamber to assist in lifting the mixture of catalyst and reactants upwardly in the reaction chamber 14. The feed gases convert to product gases while ascending in the reaction chamber 14. The blend of gases and catalyst ascend from the reaction chamber 14 through a frustoconical transition section 22 into a transport riser 32 which has a smaller diameter than an inner diameter D of the reaction chamber 14. A blend of gases and catalyst accelerate in the narrower transport riser 32 and are discharged from a primary catalyst separator 34 into the separation chamber 16. The primary catalyst separator 34 may be a riser termination device that utilizes horizontal, centripetal acceleration to separate spent catalyst from product gas. Arcuate ducts of the primary catalyst separator 34 direct the mixture of product gas and catalyst to exit from the riser 32 in a typically horizontally angular direction to centripetally accelerate causing the denser catalyst to gravitate outwardly. The catalyst loses angular momentum and falls into a separator catalyst bed 36 depicted with an upper interphase. The lighter gases ascend in the separation chamber 16 and enter into cyclones 38, 40. The cyclones 38, 40 may comprise first and second cyclonic stages of separation to further remove catalyst from product gases. The product gas is ducted to a plenum 42 from which it is discharged from the reactor 10 through a product outlet 44 in a product line 45. The superficial gas velocity in the transport riser 32 will be about 12 m/s (40 ft/s) to about 20 m/s (70 ft/s) and have a density of about 64 kg/m$^3$ (4 lb/ft$^3$) to about 160 kg/m$^3$ (10 lb/ft), constituting a dilute catalyst phase.

Catalyst separated from the product gas by the primary catalyst separator 34 drops into the dense catalyst bed 36. In an aspect, primary cyclones 38 may collect product gas from the separation chamber 16 and transport the product gas separated from catalyst to a secondary cyclone 40 to further separate catalyst from the product gas before directing secondarily purified product gas to the plenum 42. Catalyst separated from product gas in the cyclones 38, 40 is dispensed by dip legs into the dense catalyst bed 36. At this point, the separated catalyst in the separation chamber 16 is considered spent catalyst because deposits of coke are agglomerated thereon. A spent catalyst stream taken from the spent catalyst collected in the dense bed 36 in the separation chamber 16 is transported in a spent catalyst pipe 18 to a catalyst regenerator 60 to have coke burned from the catalyst to regenerate and heat the dehydrogenation catalyst.

A recycle catalyst stream is also taken from the spent catalyst collected in the dense bed 36 of the separation chamber 16 and enters the recycle catalyst pipe 24 through an inlet end 21. The recycle catalyst pipe 24 has the inlet end 21 connected to the separation chamber 16 and an outlet end 23 connected to the reaction chamber 14 for recycling catalyst to the reaction chamber. The recycle catalyst stream of the spent catalyst is recycled in the recycle catalyst pipe 22 back to the first catalyst inlet 23 in the reaction chamber 14 of the reactor 10. The first catalyst inlet 23 is the outlet end of the recycle catalyst pipe 24. The recycle catalyst stream of the spent catalyst is not regenerated before it returns to the reaction chamber 14.

The separation chamber 16 may include a disengagement can 46 that surrounds the upper end of the riser 32 and the primary separator 34. A vertical wall 47 of the disengagement can 46 is spaced apart from a shell 48 of the separation chamber to define an annulus 49. Dip legs of the cyclones 38 and 40 may be located in the annulus 49. The disengagement can 46 serves to limit travel of the product gas exiting the primary separator 34, so as to reduce its time in the reactor 10, thereby mitigating unselective cracking reactions to undesired products. The top of the disengagement can 46 may be hemispherical and feed a gas recovery conduit 50 that transports product gases to ducts 52 that are directly ducted or connected to the primary cyclones 38. The direct ducting from the disengagement can 46 to the primary cyclones 38 also prevents product gas from getting loose in the larger volume of the reactor vessel where excessive residence time may occur to permit unselective cracking. Windows in the lower section of the wall 48 of the disengagement can 46 permit catalyst in the disengagement can 46 to enter into the recycle catalyst pipe 22 or the spent catalyst pipe 18. A quench fluid such as condensed product liquid, cooled recycled gas, or even cool catalyst may be injected into the product gases through a quench nozzle 54 to cool the product gases to below cracking temperature to limit unselective cracking. Quench fluid is advantageously injected into the gas recovery conduit 50 which directs the separated product gas to a narrowed location. The gas recovery conduit 50 is in downstream communication with primary catalyst separator 34 which separates the predominance of the spent catalyst from the product gases. The primarily separated spent catalyst bypasses quenching to retain heat in the catalyst. The product gases separated from the predominance of the catalyst subjects a reduced mass of material to quenching thereby requiring less quench fluid to achieve sufficient cooling to reduce the temperature of product gas to below cracking temperature, terminating hot gas residence time.

The spent catalyst may be stripped with inert gas in a stripper vessel 58 depending from the separation vessel 16 and be transported to the catalyst regenerator vessel 60 in a spent catalyst pipe 18 to regenerate the spent catalyst into regenerated catalyst and to combust the coke if present. Fuel gas may be added to the catalyst regenerator vessel 60 to further heat catalyst by combustion. A regenerated catalyst pipe 26 transports regenerated catalyst from the regenerator 60 to the reactor 10 through a control valve thereon through the second catalyst inlet 25.

The time that feed and product gas and catalyst are in the dilute phase region 30 until the gases are separated from the catalyst is considered "hot residence time". Hot gas residence time begins when feed or product gases are in contact with catalyst outside or above the dense catalyst bed 28. We have found in PDH an increase in hot residence time can result in the loss of selectivity to desired olefins, such as propylene. After the feed begins reacting over the catalyst and feed and product gases with entrained catalyst ascend above the dense catalyst bed 28 into the dilute phase region 30, non-selective reactions can continue. The non-selective reactions in the dilute phase region 30 reduce the overall selectively of the dehydrogenation process. The bulk of the hot residence time is spent in the dilute phase region 30 before the mixture of gases and catalyst enter the transition section 22 and start to accelerate in velocity due to the decreasing inner diameter of the vessel. A method to reduce the hot residence time in the dilute phase region 30 of the reaction chamber 14 can improve the selectively and overall economics of the unit. However, reducing the hot residence time in the fast fluidized dilute phase 30 can have other adverse effects on the fluid dynamics.

Hot residence time can be reduced by decreasing the length L of the reaction chamber 14 which concomitantly reduces the length 1 of the dilute phase region 30 from the interface 29 of the dense catalyst bed to the bottom of the transition section 22. However, as 1 decreases, the dense catalyst bed begins to deteriorate and contact between feed and catalyst suffers. Without a well-established dense catalyst bed 28, feed can bypass the catalyst to avoid contact resulting in significant reductions in conversion and selectivity. The height h of the dense catalyst bed may be adjusted by increasing catalyst recycle through the recycle catalyst pipe 24 which is controlled by a control valve 27 in order to produce the desired weight hourly space velocity (WHSV) which is dependent upon the weight of catalyst in the dense catalyst bed 28. The height h of the dense catalyst bed 28 in the reaction chamber is about 1.5 m (5 ft) to about 6 m (20 ft) tall and preferably about 2.1 m (7 ft) to about 5.2 (17 ft) tall.

Increasing the superficial gas velocity may another way to decrease the hot residence time. Increasing the gas velocity, however, further impacts the fluid dynamics of the fast fluidized flow regime by requiring significantly more catalyst recycle from the separation chamber 16 to the reaction chamber 14 through the recycle catalyst pipe 24. Catalyst recycle can become impractically too high to provide sufficient catalyst to generate a dense bed at high gas velocities. Additionally, as the gas velocity is further increased, the flow regime can become unstable and change from a fast fluidized flow regime to a transport regime in which a dense catalyst bed is virtually absent. The lack of a dense catalyst bed impedes achievement of a desired WHSV in the reaction chamber 14. The catalyst to feed contact suffers in a transport regime for PDH reactions causing performance to dramatically decrease.

Accordingly, increasing the superficial gas velocity and decreasing the length L of the reaction chamber both can reduce hot catalyst residence time, but too much of either can destroy the dense catalyst bed 28 which can negate the objective of increasing selectivity and conversion. We have discovered that the key to achieving maximum selectivity and conversion is an aspect ratio of the length L of the reaction chamber 14 to the inner diameter D of the reaction chamber.

EXAMPLE

Figure 2:
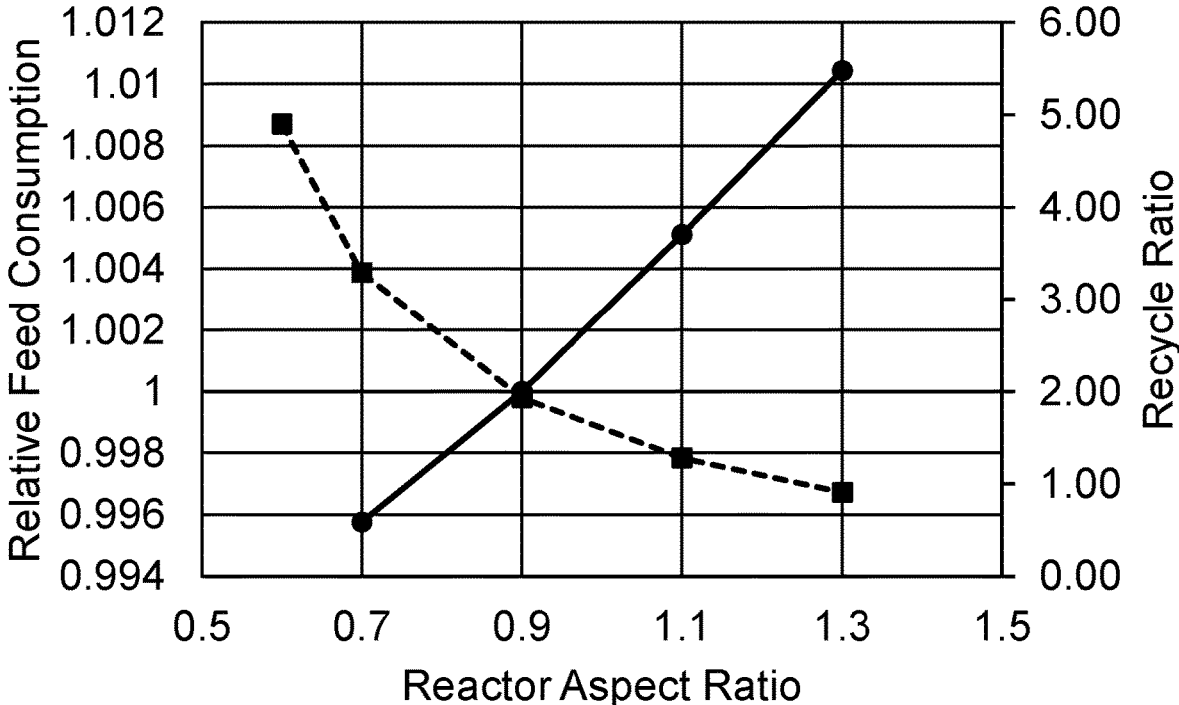
FIG. 2 is a plot of relative feed consumption vs. aspect ratio.

We simulated PDH performance for different aspect ratios at a constant conversion of 45%. Results are shown in FIG. 2 which is a plot of Relative Feed Consumption and Recycle Ratio vs. Reactor Aspect Ratio. Recycle ratio is provided on the right vertical axis and represented by solid squares and a dashed line. Lower aspect ratios having shallower dense catalyst beds resulted in higher reaction selectivity represented by lower feed consumption on the left vertical axis depicted with a solid line and solid circles. However, below a certain threshold aspect ratio, the dense catalyst bed begins to be unstable.

Figure 3:
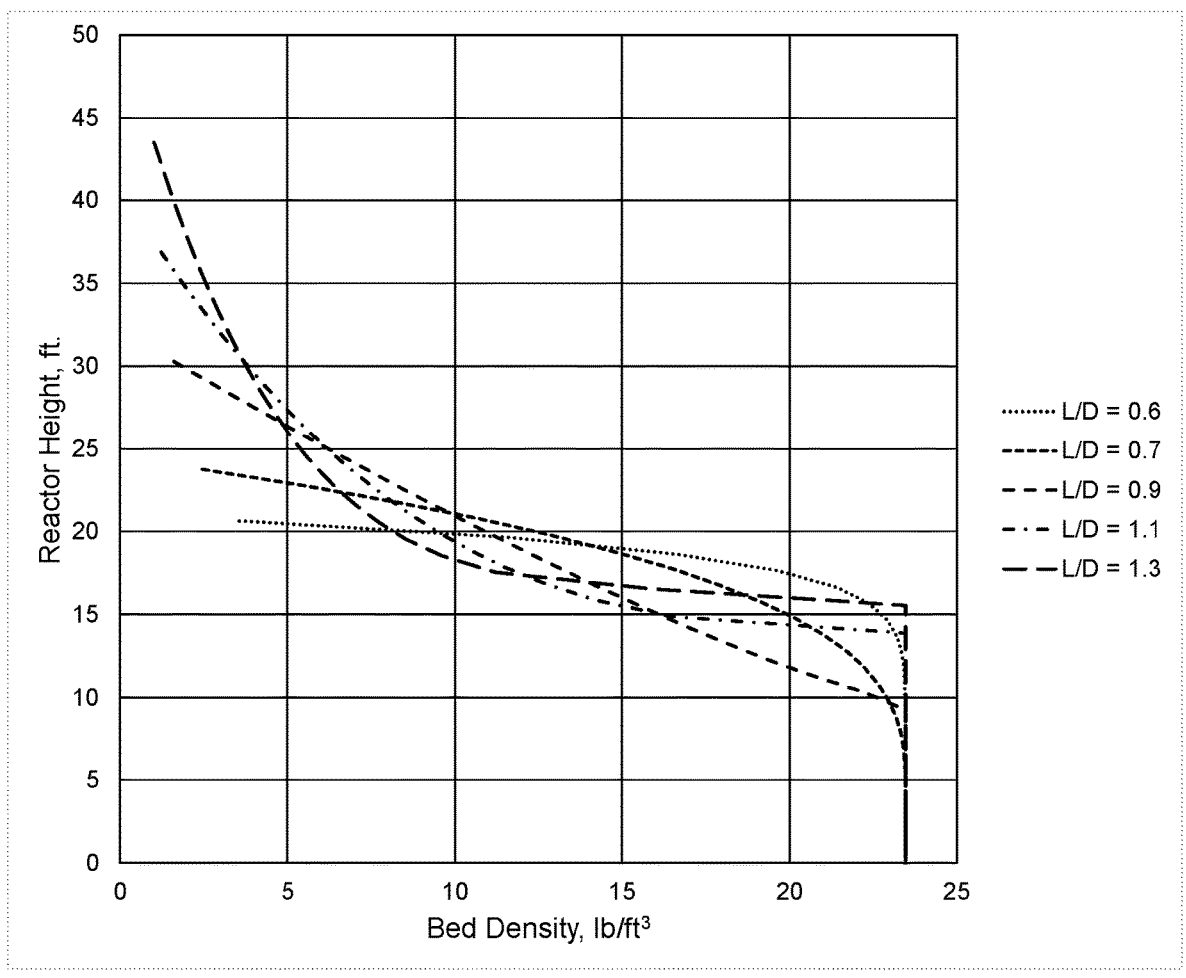
FIG. 3 is a plot of reaction chamber height vs. bed density.

We conducted additional simulations at several aspect ratios which are graphically demonstrated in FIG. 3. FIG. 3 is a plot of reactor height, L, vs. Catalyst Bed Density at several aspect ratios. The vertical portion of each curve represents generation of a dense catalyst bed of constant density for a given height h of a dense catalyst bed. At an aspect ratio of 1.1 and above, a stable dense bed of at least about 14 ft tall and a constant density of about 23.5 lb/ft' is established with a dilute catalyst region above the bed of diminishing catalyst density. At an aspect ratio of 0.9, the dense catalyst bed is reduced in height, but still with a distinct lower-density section above it. At the aspect ratio of 0.7, the curve shows the beginning disappearance of the dense bed and its merger with the dilute phase region. At an aspect ratio 0.6 a short reactor would be nearly filled to the top or flooded with a catalyst bed of near-constant density. This leads to excessive catalyst entrainment and recirculation rate with the associated fluid dynamic challenges.

Accordingly, an aspect ratio of about 0.7 to about 1.3 should be used to establish a dense catalyst bed in the reaction chamber 14 to minimize hot residence time and achieve high selectivity and conversion. Suitably, the aspect ratio should be between about 0.8 and about 1.2. Preferably, the aspect ratio should be between about 0.85 and about 1.1. The hot residence time for these discovered aspect ratios can be kept between 1.5 and 7 seconds and suitably at least 5 seconds. A gas velocity of about 1.2 m/s (4 ft/s) to about 2.4 m/s (8 ft/s) should be employed in the reaction chamber 14 and preferably between about 1.5 m/s (5 ft/s) to about 2.1 m/s (7 ft/s). The catalyst circulation ratio by weight through the recycle catalyst pipe may be between and 0.5 and 6 relative to regenerated catalyst fed to the reactor through inlet 25 from the regenerated catalyst pipe 26.

We have discovered a range of aspect ratios which are uniquely advantageous for boosting selectivity and conversion in a fluidized paraffin dehydrogenation reactor while maintaining a dense catalyst bed and minimizing hot residence time.

SPECIFIC EMBODIMENTS

While the following is described in conjunction with specific embodiments, it will be understood that this description is intended to illustrate and not limit the scope of the preceding description and the appended claims.

A first embodiment of the invention is an apparatus for contacting a feed stream with a catalyst stream comprising a reaction chamber comprising a vertical wall and defining an inner diameter and a height; a catalyst inlet for delivering the catalyst stream to the reaction chamber, a feed inlet for charging feed to the reaction chamber; and a product outlet for removing a product stream from the reaction chamber; and the reaction chamber including an aspect ratio between about 0.7 and about 1.3 for establishing a dense catalyst bed in the reaction chamber while minimizing hot residence time. An embodiment of the invention is one, any or all of prior embodiments in this paragraph up through the first embodiment in this paragraph wherein the vertical wall defines the inner diameter and the height that provides the aspect ratio. An embodiment of the invention is one, any or all of prior embodiments in this paragraph up through the first embodiment in this paragraph wherein the vertical wall is a cylinder and the height is of the vertical portion of the wall between ends that have a graduated inner diameter and the inner diameter is the inner diameter of the cylinder. An embodiment of the invention is one, any or all of prior embodiments in this paragraph up through the first embodiment in this paragraph wherein the aspect ratio is between about 0.8 and about 1.2. An embodiment of the invention is one, any or all of prior embodiments in this paragraph up through the first embodiment in this paragraph wherein the aspect ratio is between about 0.85 and about 1.1. An embodiment of the invention is one, any or all of prior embodiments in this paragraph up through the first embodiment in this paragraph further comprising a separation chamber in communication with the reaction chamber. An embodiment of the invention is one, any or all of prior embodiments in this paragraph up through the first embodiment in this paragraph further comprising a separator in the separation chamber for separating catalyst from product gas. An embodiment of the invention is one, any or all of prior embodiments in this paragraph up through the first embodiment in this paragraph further comprising a recycle pipe with an inlet end connected to the separation chamber and an outlet end connected to the reaction chamber for recycling catalyst to the reaction chamber.

A second embodiment of the invention is a process for contacting a feed stream with fluidized catalyst comprising charging the feed stream to a reaction chamber having an aspect ratio of about 0.7 to about 1.3; contacting the feed stream with a catalyst stream to produce a product gas stream and spent catalyst; and separating the product gas stream from the spent catalyst. An embodiment of the invention is one, any or all of prior embodiments in this paragraph up through the second embodiment in this paragraph further comprising recycling spent catalyst back to the reaction chamber. An embodiment of the invention is one, any or all of prior embodiments in this paragraph up through the second embodiment in this paragraph further comprising generating a dense catalyst bed in the reaction chamber of about 1.5 m (5 ft) to about 6 m (20 ft) tall. An embodiment of the invention is one, any or all of prior embodiments in this paragraph up through the second embodiment in this paragraph wherein the dense bed has a density of about 320 kg/m$^3$ (20 lb/ft') to about 480 kg/m$^3$ (30 lb/ft$^3$). An embodiment of the invention is one, any or all of prior embodiments in this paragraph up through the second embodiment in this paragraph wherein a hot residence time of the feed stream is between about 1.5 and 7 seconds. An embodiment of the invention is one, any or all of prior embodiments in this paragraph up through the second embodiment in this paragraph wherein the feed and catalyst ascend in the chamber at a gas velocity of about 1.2 m/s (4 ft/s) to about 2.4 m/s (8 ft/s). An embodiment of the invention is one, any or all of prior embodiments in this paragraph up through the second embodiment in this paragraph wherein the catalyst is recirculated at a ratio of about 0.5 to about 6 on a weight basis. An embodiment of the invention is one, any or all of prior embodiments in this paragraph up through the second embodiment in this paragraph wherein the aspect ratio is between about 0.8 and about 1.2. An embodiment of the invention is one, any or all of prior embodiments in this paragraph up through the second embodiment in this paragraph wherein the aspect ratio is between about 0.85 and about 1.1.

A third embodiment of the invention is a process for contacting a feed stream with fluidized catalyst comprising charging the feed stream to a reaction chamber having an aspect ratio of about 0.7 to about 1.3; contacting the feed stream with a catalyst stream to produce a product gas stream and spent catalyst; separating the product gas stream from the spent catalyst; and passing a portion of the spent catalyst back to the reaction chamber and another portion of the spent catalyst to a catalyst regenerator. An embodiment of the invention is one, any or all of prior embodiments in this paragraph up through the third embodiment in this paragraph further comprising generating a dense catalyst bed in the reaction chamber of about 1.5 m (5 ft) to about 6 m (20 ft) tall. An embodiment of the invention is one, any or all of prior embodiments in this paragraph up through the third embodiment in this paragraph wherein a hot residence time of the feed stream is between about 1.5 and 7 seconds.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A reactor for contacting a feed stream with a catalyst stream comprising:
   a reaction chamber comprising a vertical wall and defining an inner diameter and a height;
   a catalyst inlet for delivering said catalyst stream to said reaction chamber, a feed inlet for charging feed to said reaction chamber; and a product outlet for removing a product stream from said reaction chamber;
   said reaction chamber including an aspect ratio between about 0.7 and about 1.3 for establishing a dense catalyst bed in the reaction chamber while minimizing hot residence time,
   a separation chamber in communication with said reaction chamber; and
   a recycle pipe with an inlet end connected to said separation chamber and an outlet end connected to said reaction chamber for recycling spent catalyst to said reaction chamber.

2. The reactor of claim 1 wherein said vertical wall defines said inner diameter and said height that provides said aspect ratio.

3. The reactor of claim 1 wherein said vertical wall is a cylinder and said height is of the vertical portion of the wall between ends that have a graduated inner diameter and said inner diameter is the inner diameter of said cylinder.

4. The reactor of claim 1 wherein said aspect ratio is between about 0.8 and about 1.2.

5. The reactor of claim 4 wherein said aspect ratio is between about 0.85 and about 1.1.

6. The reactor of claim 1 further comprising a separation chamber in communication with said reaction chamber.

7. The reactor of claim 1 further comprising a separator in said separation chamber for separating catalyst from product gas.

8. The reactor of claim 7 further comprising a recycle pipe with an inlet end connected to said separation chamber and an outlet end connected to said reaction chamber for recycling catalyst to said reaction chamber.

9. A process for contacting a feed stream with fluidized catalyst comprising:
   charging said feed stream to a reaction chamber having an aspect ratio of about 0.7 to about 1.3;
   contacting said feed stream with a catalyst stream to produce a product gas stream and spent catalyst;
   separating said product gas stream from said spent catalyst; and
   recycling said spent catalyst back to said reaction chamber.

10. The process of claim 9 further comprising generating a dense catalyst bed in said reaction chamber of about 1.5 m (5 ft) to about 6 m (20 ft) tall.

11. The process of claim 10 wherein said dense bed has a density of about 320 kg/m³ (20 lb/ft³) to about 480 kg/m³ (30 lb/ft³).

12. The process of claim 9 wherein a hot residence time of said feed stream is between about 1.5 and 7 seconds.

13. The process of claim 9 wherein the feed and catalyst ascend in the chamber at a gas velocity of about 1.2 m/s (4 ft/s) to about 2.4 m/s (8 ft/s).

14. The process of claim 9 wherein said catalyst is recirculated at a ratio of about 0.5 to about 6 on a weight basis relative to regenerated catalyst fed to the reactor.

15. The process of claim 9 wherein said aspect ratio is between about 0.8 and about 1.2.

16. The process of claim 15 wherein said aspect ratio is between about 0.85 and about 1.1.

17. A process for contacting a feed stream with fluidized catalyst comprising:

charging said feed stream to a reaction chamber having an aspect ratio of about 0.7 to about 1.3;

contacting said feed stream with a catalyst stream to produce a product gas stream and spent catalyst;

separating said product gas stream from said spent catalyst;

passing a portion of said spent catalyst back to said reaction chamber and another portion of said spent catalyst to a catalyst regenerator; and generating a dense catalyst bed in said reaction chamber of 1.5 m (5 ft) to 6 m (20 ft) tall.

18. The process of claim 17 wherein a hot residence time of said feed stream is between about 1.5 and 7 seconds.

* * * * *